United States Patent [19]

Muto

[11] Patent Number: 4,468,216
[45] Date of Patent: Aug. 28, 1984

[54] IRRIGATION SUCTION CATHETER

[76] Inventor: Rudolph Muto, 24 Williams St., Andover, Mass. 01810

[21] Appl. No.: 380,053

[22] Filed: May 20, 1982

[51] Int. Cl.³ .............................................. A61M 3/00
[52] U.S. Cl. ..................................................... 604/43
[58] Field of Search ....................... 604/19, 27, 28, 30, 604/35, 39, 40, 43, 128, 129, 165

[56] References Cited

U.S. PATENT DOCUMENTS

| | | | |
|---|---|---|---|
| 1,884,970 | 5/1916 | Larssen | 604/39 |
| 1,889,425 | 11/1932 | Sorensen | 604/35 |
| 2,148,541 | 2/1939 | Dierker | 604/35 |
| 3,766,916 | 10/1973 | Moorehead et al. | 604/165 |
| 4,096,860 | 6/1978 | McLaughlin | 604/30 |
| 4,294,251 | 10/1981 | Greenwald et al. | 604/43 |

Primary Examiner—John D. Yasko
Attorney, Agent, or Firm—Pearson & Pearson

[57] ABSTRACT

An irrigation suction catheter comprises an elongated flexible outer tube having a proximal end connectable to a source of vacuum, a distal end having a suction inlet across the terminal tip and an aperture, near the proximal end opening to the atmosphere, but closable by the thumb or finger to close the suction circuit. Sleeved within the suction tube is an elongated flexible irrigation tube having a proximal end connectable to pressurized irrigation fluid, a distal end extending beyond the suction inlet, to form a projecting flexible tip with an irrigation discharge outlet at the terminus of the tip. A vortical circulation is set up by the irrigation outlet to guide dislodged debris into the suction inlet, when both suction and irrigation are applied simultaneously. The inner, flexible irrigation tube, with its projecting terminal tip may also be sleeved in the hollow bore of a fiber optic endoscope, or in a bronchoscope, gastroscope, colonoscope or other similar devices. The projecting distal end of the irrigation tube is easily bendable and free to move sidewise or axially within the annular suction inlet opening to dislodge particles and free the opening of plugging.

7 Claims, 4 Drawing Figures

000
IRRIGATION SUCTION CATHETER

BACKGROUND OF THE INVENTION

It has heretofore been proposed to provide a suction catheter for removing undesired particles, mucous, blood or similar debris from a cavity in the human body, such catheters usually comprising an elongated, flexible tube having one end connectable to a source of vacuum, the other end forming an insertable tip with a suction inlet therein and an opening to atmosphere near the proximal end which can be selectively closed by the thumb of the surgeon to seal the tube and apply suction.

One type of suction catheter is disclosed in U.S. Pat. No. 3,375,828 to Sheridan of Apr. 2, 1968 in which a rolled up sleeve can be unrolled over the airway control aperture to apply suction in the nose, mouth, pharynx, trachea, bronchi, or other cavity in the body of a patient.

In U.S. Pat. No. 3,982,540 to Ross of Sept. 28, 1976 a multilumen tube is disclosed in which there are a plurality of spaced suction apertures in the outside wall of the negative pressure tube and a plurality of spaced positive pressure apertures, each located behind a suction aperture, to dislodge particles blocking the suction apertures.

In U.S. Pat. No. 4,014,333 to McIntyre of Mar. 29, 1977, a combined suction and irrigation instrument is disclosed for use in opthalmic surgery wherein an inner and an outer tube of straight rigid material are provided in fixed relationship, the suction tip of the inner tube projecting beyond the irrigation tip of the outer tube, so that the debris-receiving, suction inlet opening is in front of, and beyond the annular pressurized irrigation outlet opening.

The above mentioned Ross and McIntyre patents, which disclose combined suction and irrigation, both teach the placement of the pressurized liquid outlets in rear of the suction inlets and both teach a fixed relationship of the irrigation tube and the suction tube, so that the irrigation tube cannot be easily and quickly removed.

In addition to the above patents, there is a line of road vacuum cleaning apparatus, typified in the patents listed below in which there are debris-receiving inlets and/or suction inlets combined with air pressure outlets for dislodging trash, but these patents also teach placing the air outlet in rear of, or flush with, the suction, or debris-receiving, inlet.

U.S. Pat. No. 2,990,019 to Finn of June 27, 1961
U.S. Pat. No. 3,221,358 to Dickson of Dec. 7, 1965
U.S. Pat. No. 3,447,188 to Maasbery of June 3, 1969

SUMMARY OF THE INVENTION

In this invention, an elongated flexible, outer, suction tube of predetermined inside diameter and length has an elongated, flexible, inner irrigation tube of lesser outside diameter and greater length than the suction tube, substantially coaxially and concentrically sleeved therewithin to form an annular suction passage therebetween.

The distal end of the irrigation tube has a bendable, flexible, terminal tip extending beyond the annular suction inlet opening of the outer suction tube, for about one half inch, and has an irrigation discharge, or outlet, opening extending transversely across the end thereof, the tip being freely movable sidewise to conform to the contour of any passage in which inserted while also guiding the following tip of the suction tube.

The proximal end of the suction tube is connected to a Y shaped coupling, one branch of which connects to a source of suction and there being an airway, thumb-closable, aperture, between the coupling and the source, to regulate and control the application of suction.

The proximal end of the irrigation tube, extends through the other branch of the Y coupling to a finger grip having a tapered nipple slidably fitted in the bore of the branch and thence is connected to a source of irrigation fluid, such as a pressurized source of a saline solution or similar liquid.

It is thus possible to insert the tips of the irrigation suction catheter into a cavity and to simultaneously discharge irrigation fluid from a location in front of and beyond the debris-receiving, annular, suction inlet, while suction is being applied at said inlet to thus produce a vortical circulation within the cavity. Particles are thereby dislodged hydraulically by the outflowing axial stream from the irrigation tip, circulated around the space in front of the suction inlet in a vortex and returned to the axial centre for removal through the annular suction passage.

When irrigation is not required or needed, the irrigation tube is withdrawn by the finger grip, and an elastomeric cap placed over the other branch of the Y coupling so that the device becomes an ordinary suction catheter only, until irrigation is needed.

DESCRIPTION OF A PREFERRED EMBODIMENT

Figure 1:
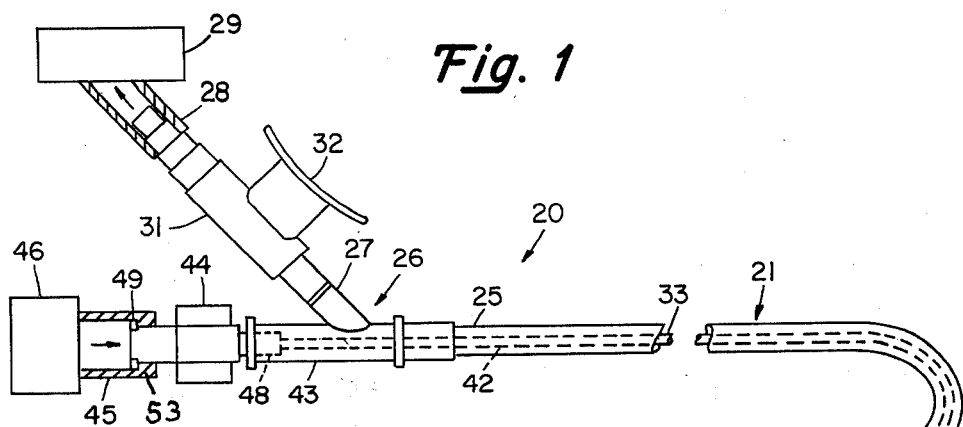
FIG. 1 is a side elevation of an irrigation suction catheter of the invention with parts broken away.

As shown in the drawing, the irrigation suction catheter 20 of the invention includes an elongated, flexible, outer suction tube 21 of predetermined length and inside diameter having a distal end 22 with a debris receiving and suction inlet 23 extending transversely across the terminal tip 24 thereof.

The proximal end 25 of suction tube 21 is connected to a Y coupling 26, one branch 27 thereof being connected by conduit 28 to a source of suction 29 such as hospital suction or a vacuum pump. A thumb operable, airway member 31 has an opening 32, to atmosphere and is located between the source 29 and the branch 27 near the proximal end 25 so that the surgeon may regulate and control the application of suction in suction inlet 23.

An elongated flexible, inner irrigation tube 33 of predetermined length greater than the length of suction tube 21 and of predetermined outside diameter substantially less than the inside diameter of suction tube 21 is slidably sleeved within the tube 21 and is substantially coaxial and concentric therewithin. The irrigation tube 33 thus forms an annular suction inlet 34 and an annular suction passage 35 between tubes 21 and 33, the annular suction inlet 34 extending transversely across the terminal tip 24 except for the portion occupied by tube 33.

The irrigation tube 33 has a distal end 36 with a terminal tip 37 extending in front of, and beyond the annular inlet 34 for about one half inch and terminating in the irrigation liquid outlet 38 which extends transversely thereacross and is normally aligned centrally along the longitudinal axis of the bore 39 of suction tube 21 but easily bendable sidewise to conform to the shape of a cavity 41 in which it is inserted and to serve as a guide for the suction tip 24.

The proximal end 42 of irrigation tube 33 passes through the other branch 43 of the Y coupling 26 to a hollow finger grip 44 and thence is connected by a conduit 45 to a source of pressurized irrigation fluid 46 such as a saline solution 47 in a pressurized tank or a pump and tank apparatus not shown. The finger grip 44 includes a hollow tapered nipple 48 which slidably fits in the bore of the branch 43 and the branch 43 includes a peripheral rim flange 49 over which a cap 51 of elastomeric material may be fitted.

In operation, as shown in FIG. 1 the irrigation suction catheter 20 may have the outer tube connected to suction source 29 and the inner tube connected to pressurized irrigation liquid source 46 and the tips 24 and 37 inserted into a cavity 41 in a manner well known in the medical art. The flexible tip 37 will tend to guide the larger flexible tip 24 during insertion and when fully emplaced the surgeon can close the airway opening 32 so that both suction and irrigation occur simultaneously. It should be noted that prior to this invention, it has been the custom to first insert a separate irrigation tube to dislodge particles 52 from a cavity 41, then to withdrawn the irrigation tube and then to insert a suction catheter in the hope that the particles will still remain dislodged and be removable by suction.

Figure 2:
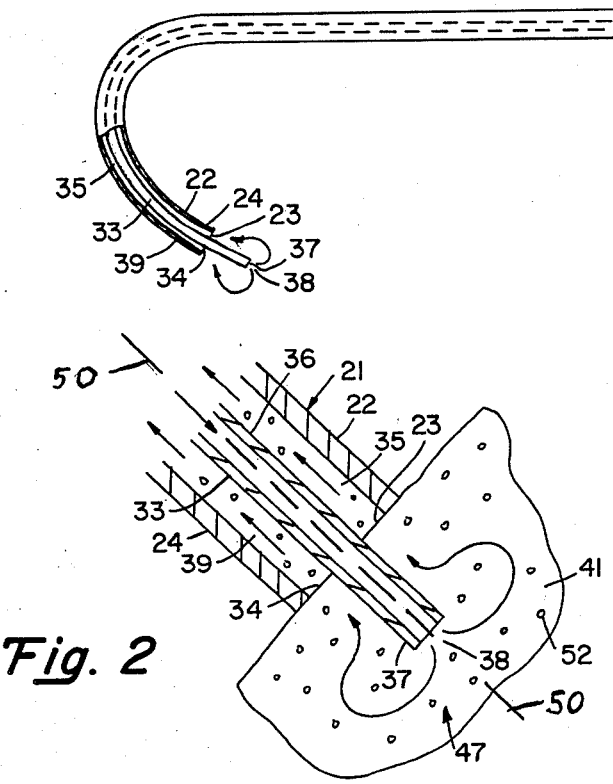
FIG. 2 is an enlarged, fragmentary, diagramatic side elevation illustrating the vertical circulation which dislodges particles.

With the catheter 20 of this invention, irrigation takes place simultaneously with suction, and from a discharge opening 38 in front of, and beyond an annular suction and debris-receiving inlet 34 which results in vortical circulation as shown by the arrows in FIGS. 1 and 2. The dislodged particles 52 thus travel outwardly around the walls of the cavity 41 first away from the central longitudinal axis 50 of the bore 39 of suction tube 21 and then back inwardly toward the axis for rapid removal through annular passage 35 without having time to again settle in place.

Figure 3:
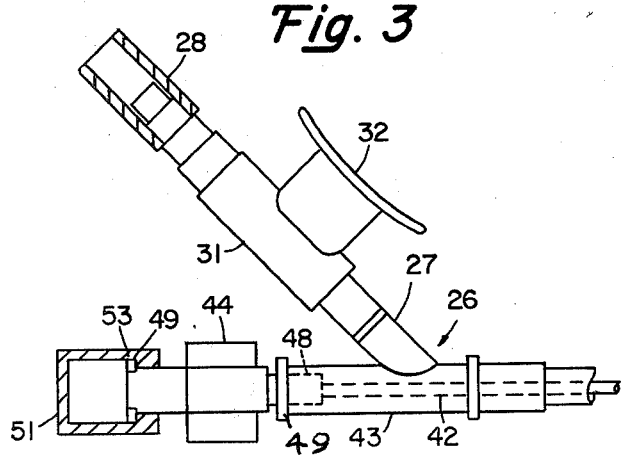
FIG. 3 is a fragmentary view similar to FIG. 1 showing the irrigation tube capped and FIG. 4 is a view similar to FIG. 3 showing the irrigation tube completely removed and the branch of the Y coupling capped.
Figure 4:
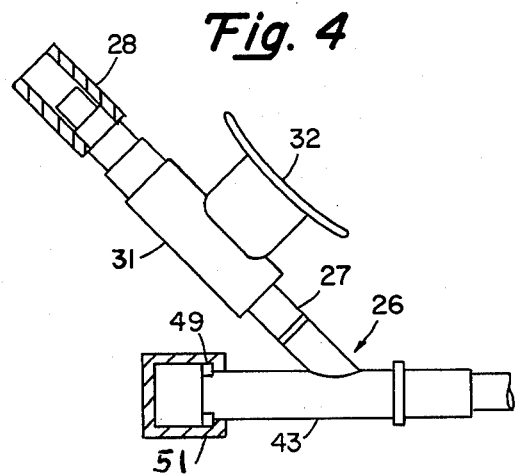

As shown in FIG. 3, if irrigation is not required the conduit 45 can be removed and the cap 51 placed over the rim 53 of the finger grip 44 to seal the branch 43 with the irrigation tube 33 in place. If no irrigation tube is needed, the tube 33 is slidably removed by the finger grip 44 and the cap 51 placed over the rim 53 of the finger grip 44 to seal the branch 43 with the irrigation tube 33 in place. If no irrigation tube is needed, the tube 33 is slidably removed by the finger grip 44 and the cap 51 fitted over the rim 49 of branch 43 to also seal the branch and convert the device to a suction catheter only.

I claim:

1. An irrigation suction catheter comprising:
a flexible, elongated suction tube of predetermined diameter and length having a distal end with a debris receiving suction inlet opening extending transversely across the terminal tip thereof, a proximal end connected by one branch of a Y coupling to a source of vacuum and a thumb operable aperture member located near said proximal end, between said vacuum source and said Y coupling for controlling the application of suction at said inlet opening and;
a flexible elongated liquid irrigation tube of predetermined diameter substantially less than the diameter of said suction tube, said liquid irrigation tube being sleeved within, and substantially coaxial with, said suction tube to form therebetween an annular suction passage, said liquid irrigation tube being of greater length than the length of said suction tube and having a distal end, with a liquid outlet opening extending transversely across the terminal tip thereof, said tip projecting a spaced distance in front of, and beyond, said suction inlet opening;
said projecting distal end of said irrigation tube forming an annular debris receiving suction inlet therearound and being freely bendable, and sidewise movable therein to clear said inlet of foreign material and avoid plugging of said annular opening and passage;
said liquid irrigation tube having a proximal end extending through the other branch of said Y coupling to a finger grip and thence to a source of liquid under pressure;
pressurized liquid discharge from said liquid outlet simultaneously with application of suction in said debris-receiving inlet creating a vortical circulation, in a cavity in which said catheter is inserted, to dislodge particles for suction removal.

2. A suction catheter as specified in claim 1 wherein:
said suction catheter includes a cap of elastomeric material fitting over the end of the other branch of said Y coupling and wherein said liquid irrigation tube and finger grip are slidably removable from within said suction tube when not desired for use in irrigation.

3. A suction catheter as specified in claim 1 wherein:
said finger grip has a forwardly projecting tapered nipple for slidably fitting within the other branch of said Y coupling to seal the same against admission of ambient air.

4. A suction catheter as specified in claim 1 wherein:
the projecting distal end of said liquid irrigation tube is axially movable within said suction inlet opening so that it can be manipulated by reciprocation of said finger grip relative to said Y coupling to disturb particles for vortical circulation and suction removal.

5. An irrigation suction catheter comprising:
an outer, elongated, suction tube having an inner, elongated, liquid irrigation tube coaxially and concentrically sleeved therewithin, said irrigation tube being of substantially less outside diameter than the inside diameter of said suction tube to form an annular suction passage therearound;
said irrigation tube being of greater length than said suction tube, said suction tube having an insertable, distal terminal end with a suction inlet extending transversely thereacrss and said irrigation tube having a distal end with a terminal, tip projecting a spaced distance beyond said suction inlet with an irrigation outlet extending transversely thereacross,
said distal end of said irrigation tube forming an annular, debris receiving suction inlet therearound and being freely bendabe, axially movable and sidewise movable therein to clear said inlet of plugging;

means for applying suction through said suction tube to said suction inlet and;

means for simultaneously discharging pressurized irrigation fluid from said irrigation outlet;

whereby a vortical circulation is achieved in the cavity in which said tips are inserted to dislodge debris for removal through said suction inlet and passage.

6. In a suction catheter of the type having an elongated flexible tube with a suction inlet in the terminal tip of the distal end, a proximal end connectable to a source of vacuum and a means for connecting said tube to atmosphere, near said proximal end the combination of:

an elongated flexible irrigation tube, of less outside diameter than the inside diameter of said suction tube, coaxially and concentrically sleeved within said suction tube to form an annular suction passage therearound;

said irrigation tube having a proximal end connectable to a source of fluid under pressure; a finger grip near said proximal end and beyond the proximal end of said suction tube; and having a distal end, which projects a spaced distance beyond the suction inlet of said suction tube to form a flexible, terminal irrigation tip with an irrigation discharge outlet extending transversely across the end of said tip;

said projecting distal end of said irrigation tube forming an annular debris-receiving suction inlet therearound and being freely movable sidewise therein, so that flexing of said terminal tip bends said distal end to continually clear said annular inlet of foreign particles.

7. An irrigation suction catheter comprising:

a flexible, elongated, outer, suction catheter tube of predetermined diameter, having a distal end opening and a proximal end;

a flexible elongated, inner, irrigation tube of predetermined diameter, substantially less than the diameter of said catheter, sleeved within said catheter, and having a distal end projecting beyond the distal end opening of said catheter, and a proximal end;

said projecting distal end being flexible, bendable and movable sidewise and axially within the distal end opening of said catheter to form an annular debris-receiving suction inlet therewithin and to keep said inlet free of plugging when manipulated from the proximal end thereof or flexed by contact in a cavity of the body.

* * * * *